(12) United States Patent
Geiger

(10) Patent No.: US 7,054,001 B2
(45) Date of Patent: May 30, 2006

(54) SUPPORT FOR A MICROTITER PLATE

(75) Inventor: Alfred Geiger, Hausen am Albis (CH)

(73) Assignee: Tecan Trading AG, Mannendorf (CH)

( * ) Notice: Subject to any disclaimer, the term of this patent is extended or adjusted under 35 U.S.C. 154(b) by 208 days.

(21) Appl. No.: 10/362,257

(22) PCT Filed: Aug. 29, 2001

(86) PCT No.: PCT/EP01/09950

§ 371 (c)(1),
(2), (4) Date: Feb. 21, 2003

(87) PCT Pub. No.: WO02/21145

PCT Pub. Date: Mar. 14, 2002

(65) Prior Publication Data

US 2003/0174394 A1     Sep. 18, 2003

(30) Foreign Application Priority Data

Sep. 5, 2000   (EP) ................................ 00119174

(51) Int. Cl.
*G01N 21/01*   (2006.01)
(52) U.S. Cl. ........................................ 356/244
(58) Field of Classification Search ......... 356/244–246
See application file for complete search history.

(56) References Cited

U.S. PATENT DOCUMENTS

| | | | | | |
|---|---|---|---|---|---|
| 4,645,316 | A | * | 2/1987 | Ohyama | 248/481 |
| 4,710,031 | A | * | 12/1987 | Kelly et al. | 356/440 |
| 5,295,700 | A | * | 3/1994 | Crews et al. | 279/5 |
| 5,328,019 | A | * | 7/1994 | Boutet et al. | 198/624 |
| 5,615,054 | A | * | 3/1997 | Lang et al. | 359/844 |
| 5,993,746 | A | * | 11/1999 | Priha et al. | 422/104 |

FOREIGN PATENT DOCUMENTS

DE     3128394 A1 *  7/1981

* cited by examiner

*Primary Examiner*—Michael P. Stafira
(74) *Attorney, Agent, or Firm*—Notaro & Michalos PC

(57) ABSTRACT

A support for a microtiter plate has a base and a supporting plate connected to the base by a fixable ball and socket joint so the plate can tip and/or rotate in a limited way. The center of rotation of the joint lies at the upper side of the support plate and the ball and socket joint are made up of a socket connected to the base, and a ball mounted in the socket and connected to the plate. The ball has a connecting piece shaped onto the lower side of the ball, which projects through an opening of the socket. The connecting piece supports a stop on which a clamping part is supported. The clamping part presses against the outside of the socket and may be pressed against the socket to fix the ball and socket joint.

14 Claims, 9 Drawing Sheets

US 7,054,001 B2

SUPPORT FOR A MICROTITER PLATE

RELATED ART

A support for microtiter plates according to the species is known (see U.S. Pat. No. 5,592,289), on which the plates are positioned in that two perpendicular edges of the microtiter plate are pressed against stop surfaces by springs acting on the opposite edges. In a similar embodiment (WO 99/15905), the microtiter plate is pressed against the stop surfaces by a lever acting elastically on a corner. In both cases, it is the positions of the edges of the microtiter plate pressing against the stops which are fixed on the support. This has the disadvantage that tolerances of the microtiter plate may have an effect over its entire length and width. For the processing of microtiter plates having a large number of very small cavities, as is increasingly typical, this may lead to difficulties in the regions which border the edges opposite the stops.

DESCRIPTION OF THE INVENTION

The present invention is based on the object of specifying a support according to the species which allows reliable and exact processing of the liquid samples even if microtiter plates having a large number of very small cavities are used.

This object is achieved by the features in the characterizing part of claim 1. In the support according to the present invention, the microtiter plate is centered, i.e., it is the position of its centerpoint which is fixed on the support. Therefore, tolerances may only have an effect over half of the length and width of the microtiter plate. The support according to the present invention therefore particularly allows reliable automatic processing of standard microtiter plates having 48×32 cavities.

BRIEF DESCRIPTION OF THE DRAWINGS

In the following, the present invention is described in more detail on the basis of figures which merely illustrate one exemplary embodiment.

EMBODIMENTS OF THE INVENTION

Figure 1:
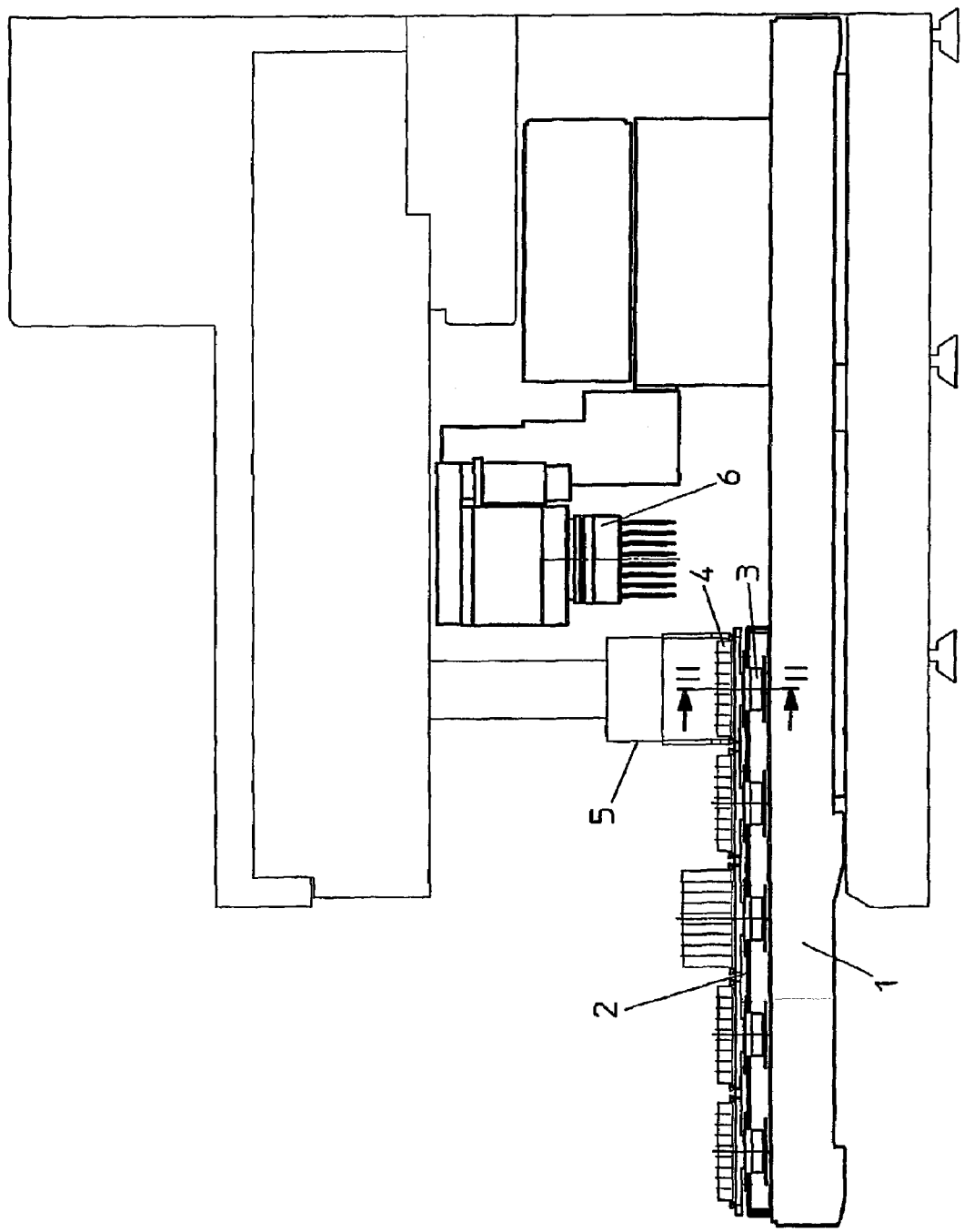
FIG. 1 shows a side view of a workstation having supports according to the present invention.
Figure 2:
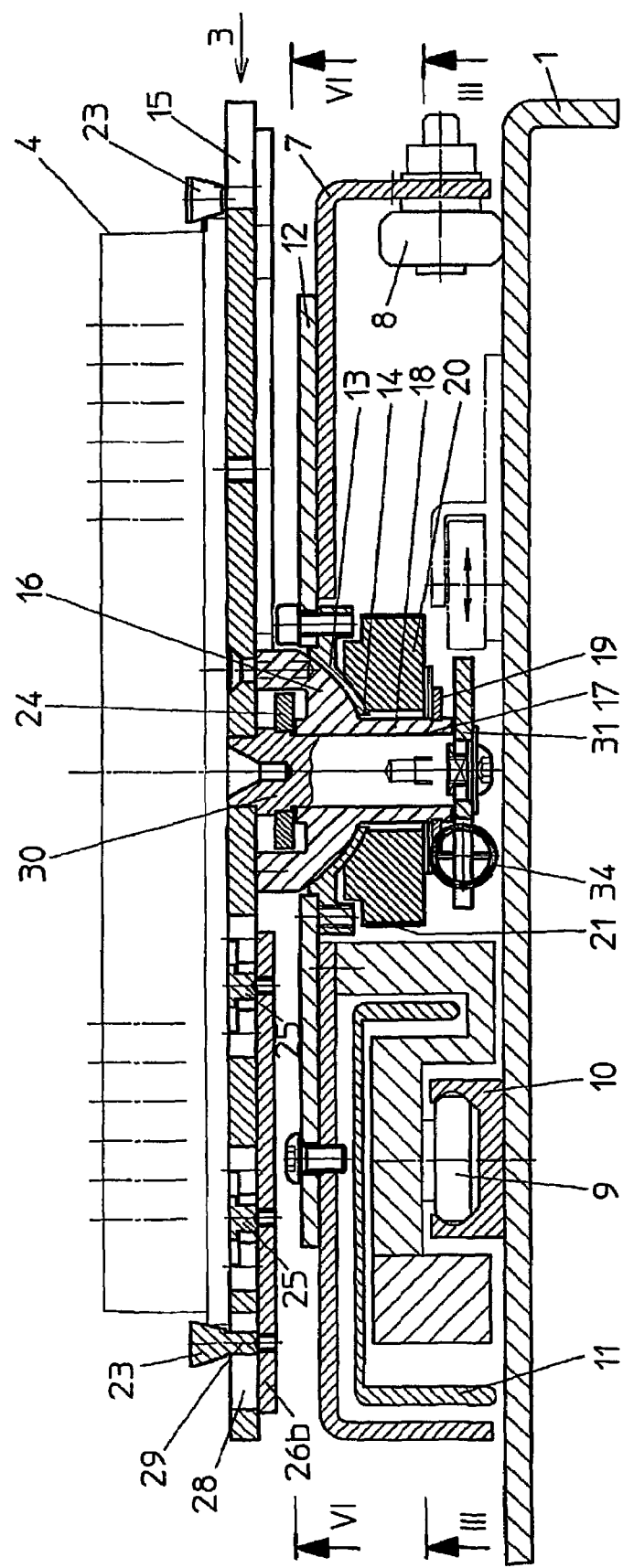
FIG. 2 shows an enlargement of a section approximately along II—II in FIG. 1 through a support according to the present invention with a locked microtiter plate and its anchoring on the workstation—in the region of the support plate, the section II—II follows in FIG. 4.

A workstation has (FIG. 1) a table 1, on which multiple parallel slide blocks 2 (one of them is shown in section in FIG. 2), each having multiple supports 3, which each support a microtiter plate 4, are mounted so they are movable lengthwise. A manipulator 5 is suspended above the table 1 so it may be raised and lowered as well as moved laterally, i.e., transverse to the lengthwise direction of the slide blocks 2, as is a pipetting head 6, which may also be raised and lowered. At a loading and unloading point, the manipulator 5 may lift a microtiter plate 4 from a support 3 on the slide block 2, move it laterally, and set it down on a support of another slide block or at another point of the table 1. If a support having a microtiter plate is pushed under the pipetting head through lengthwise movement of the corresponding slide block 2, the head may be lowered to the microtiter plate and deliver sample liquid into the cavities of the microtiter plate or suction reagents out of the cavities.

Figure 3:
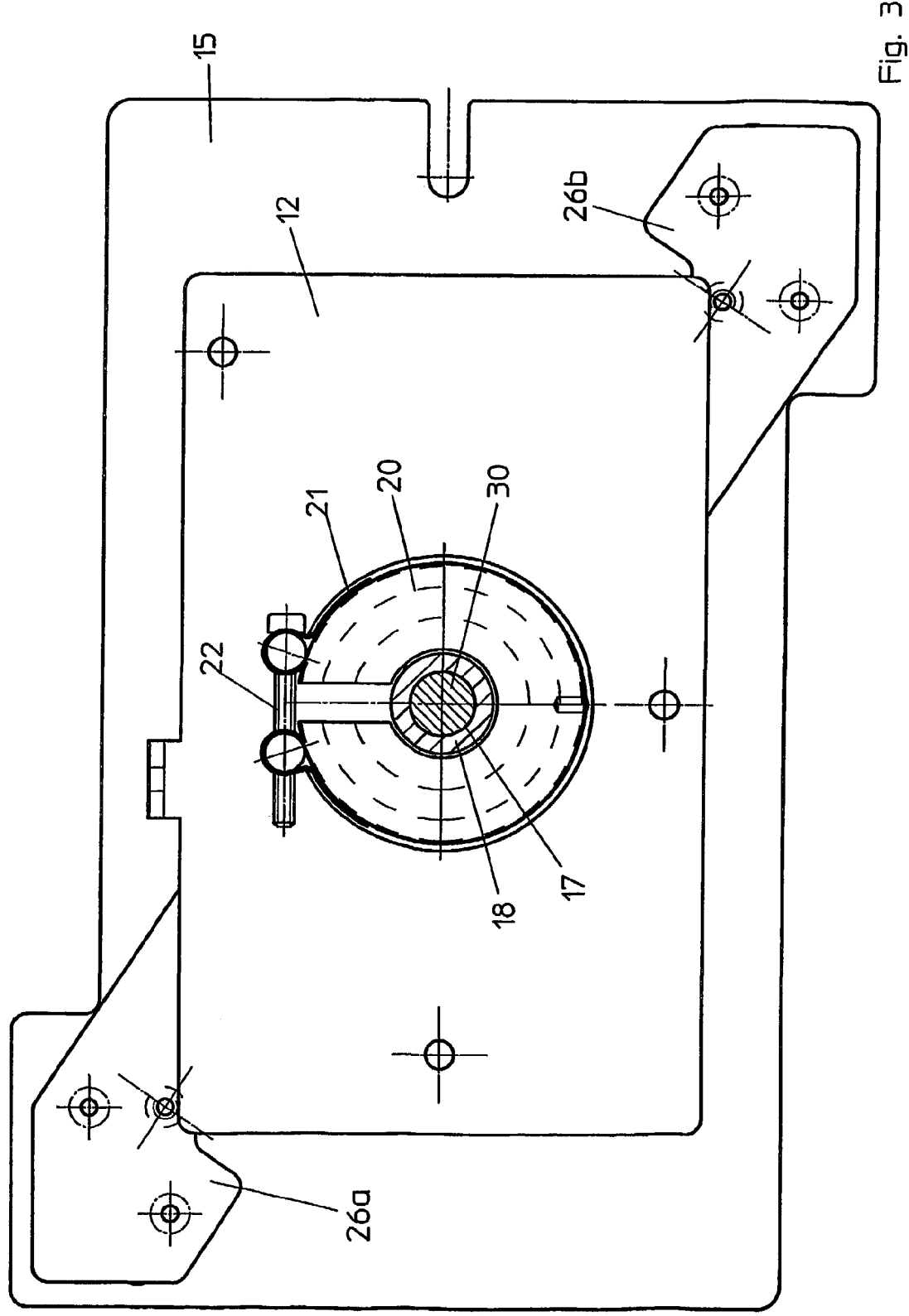
FIG. 3 shows a section along III—III in FIG. 2 through the support according to the present invention with a locked microtiter plate.

The slide block 2 has (FIGS. 2, 3) a support profile 7, which is provided on one side with support rollers 8, using which the slide block 2 is movably supported on the table 1, and on the other side with guide rollers 9, which engage with a guide rail 10 attached to the table 1. The guide rail 10 and the guide rollers 9 are protected by a cover profile 11, also anchored on the table 1. The support 3 has (FIG. 2) a base which is implemented as a rectangular bearing plate 12 and is attached to the support profile 7. A shell-shaped socket 13 made of metal, e.g., aluminum, having a circular central opening 14 is attached in a central opening of the base.

A support plate 15, also approximately rectangular, which supports the microtiter plate 4, has a ball 16 made of plastic, e.g., polyoxymethylene, on its lower side, which fits snugly in the socket 13 in such a way that a part of its outer surface shaped like a partial sphere presses against the correspondingly shaped inner surface of the socket 13. The ball 16 has a central vertical through hole 17, which continues through an extension shaped onto the lower side, a tubular connecting piece 18, which projects through the opening 14 of the socket 13 with lateral play.

Near its lower end, the connecting piece 18 has an annular stop 19, on which a clamping part implemented as a clamping ring 20 made of an elastic material, preferably plastic such as polypropylene, is supported. A part of the upper side of the clamping ring 20 shaped like a partial sphere presses snugly against the correspondingly shaped outer surface of the socket 13. The clamping ring is surrounded by a clip 21 which presses against its outside, and which may be tensioned using a fixing screw 22.

When the clip 21 is loose, the ball 16 lies loosely in the socket 13, so that the support plate 15 is freely rotatable over a spatial angle range whose limits are determined by the outside of the connecting piece 18 and the edge of the opening 14 in the socket 13, the center of rotation being at the height of the upper side of the support plate 15, in fact at its centerpoint. The support plate 15 is therefore particularly rotatable around a vertical axis through the centerpoint and tiltable around arbitrary axes running, for example, in the lengthwise direction or transverse direction at the height of the upper side of the support plate 15.

In contrast, when the clip 21 is tensioned, the clamping ring 20 exerts pressure against the outside of the socket 13, which is clamped between the ring and the ball 16. The joint is therefore clamped and the spatial alignment of the support plate 15 in relation to the bearing plate 12 and therefore also the slide block 2 is fixed. The ball and socket joint formed by the socket 13 and the ball 16 thus allows adjustment of the support 15 to a position, fixable by tensioning the clip 21 using the fixing screw 22, which is tailored precisely to other components, such as the manipulator 5 and, above all, the pipetting head 6.

Figure 4:
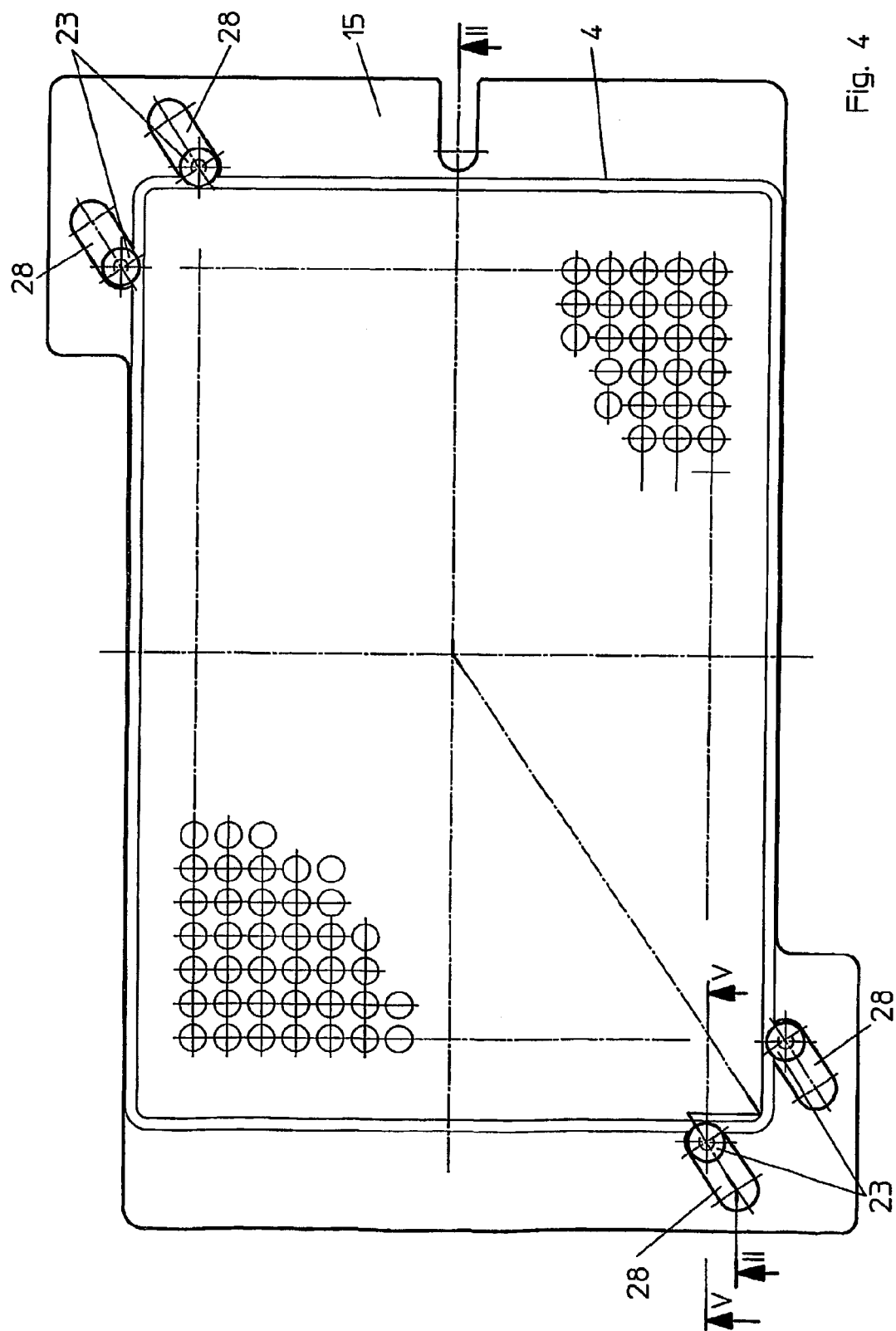
FIG. 4 shows a top view of the support according to the present invention with a locked microtiter plate.
Figure 5:
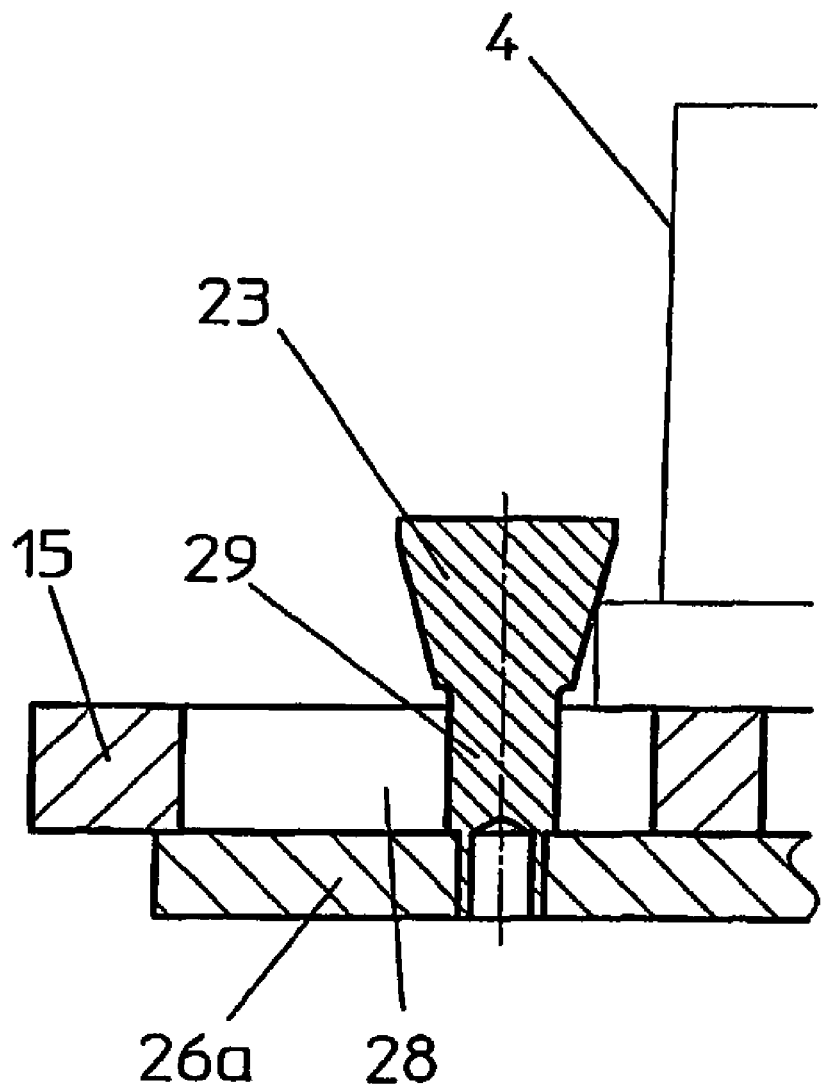
FIG. 5 shows a partial section along V—V in FIG. 4 through the support according to the present invention with a locked microtiter plate.

The support plate 15 has (see also FIGS. 4, 5) two centering stops positioned in opposing corners on the upper side, which may be moved outward diametrically opposite one another along a diagonal which connects them, so that they always have the same distance from the centerpoint, which is coincident with the center of rotation of the support plate 15. Each of the centering stops comprises two centering heads 23, tapering downward, which are at a distance to one another transversely to the diagonal described.

Figure 6A:
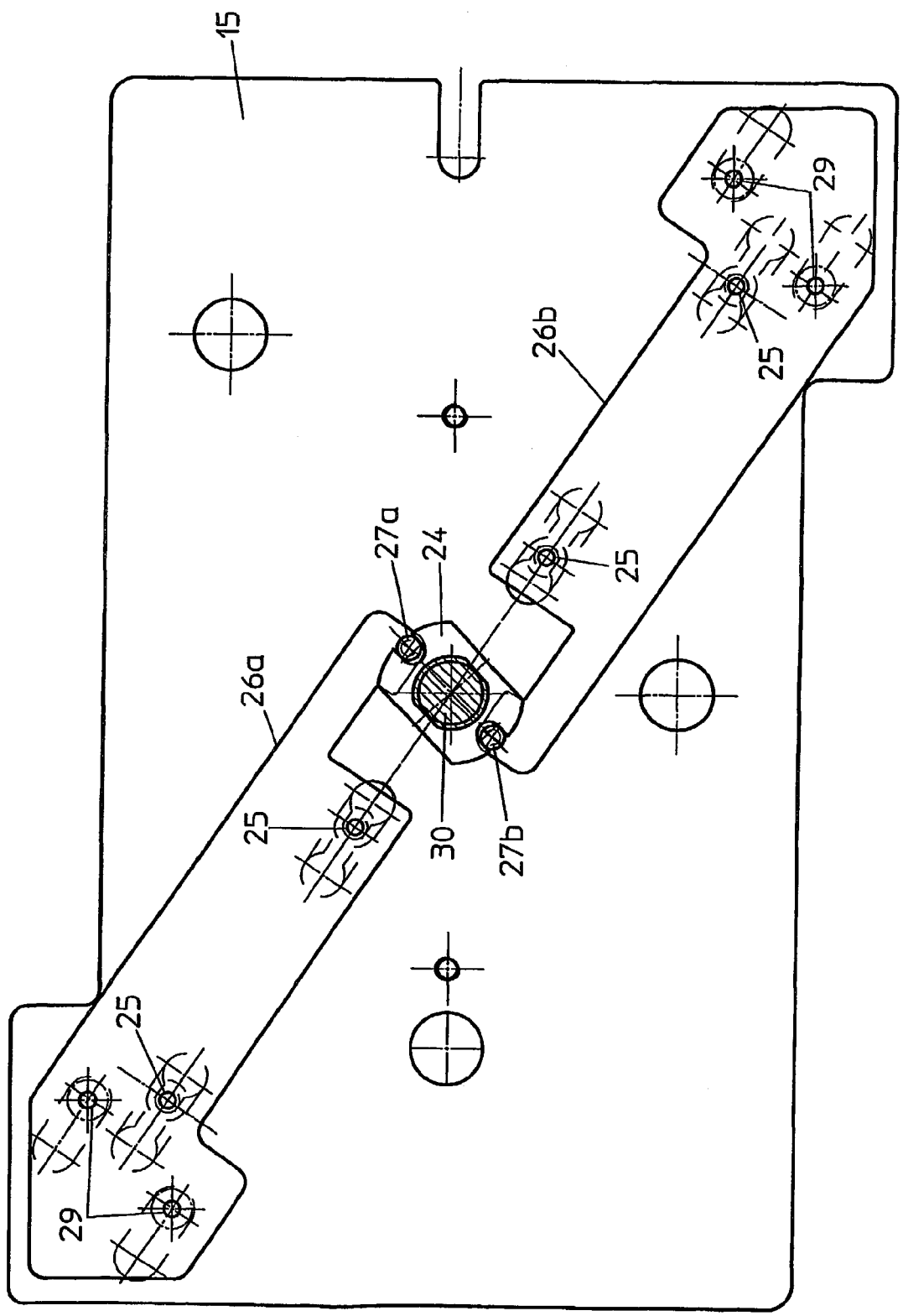
FIG. 6a shows a section along VI—VI in FIG. 2 through the support according to the present invention with a locked microtiter plate.

The diametrically opposing motion is (see FIG. 6a) controlled by a coupling attached to the lower side of the support plate 15, which includes a coupling lever 24, which is rotatably connected to the support plate 15 around the axis running perpendicularly through the centerpoint of the support plate, as well as two sliders 26a, b, mounted on two guide pins 25 so they are diagonally displaceable, which each engage with carrier pins 27a, b in recesses introduced diametrically opposite one another on the coupling lever 24. On their outer ends, the sliders 26a, b support the centering heads 23, which are attached to the support plate 15 via shanks 29 projecting into slots 28 in the plate.

Figure 7A:
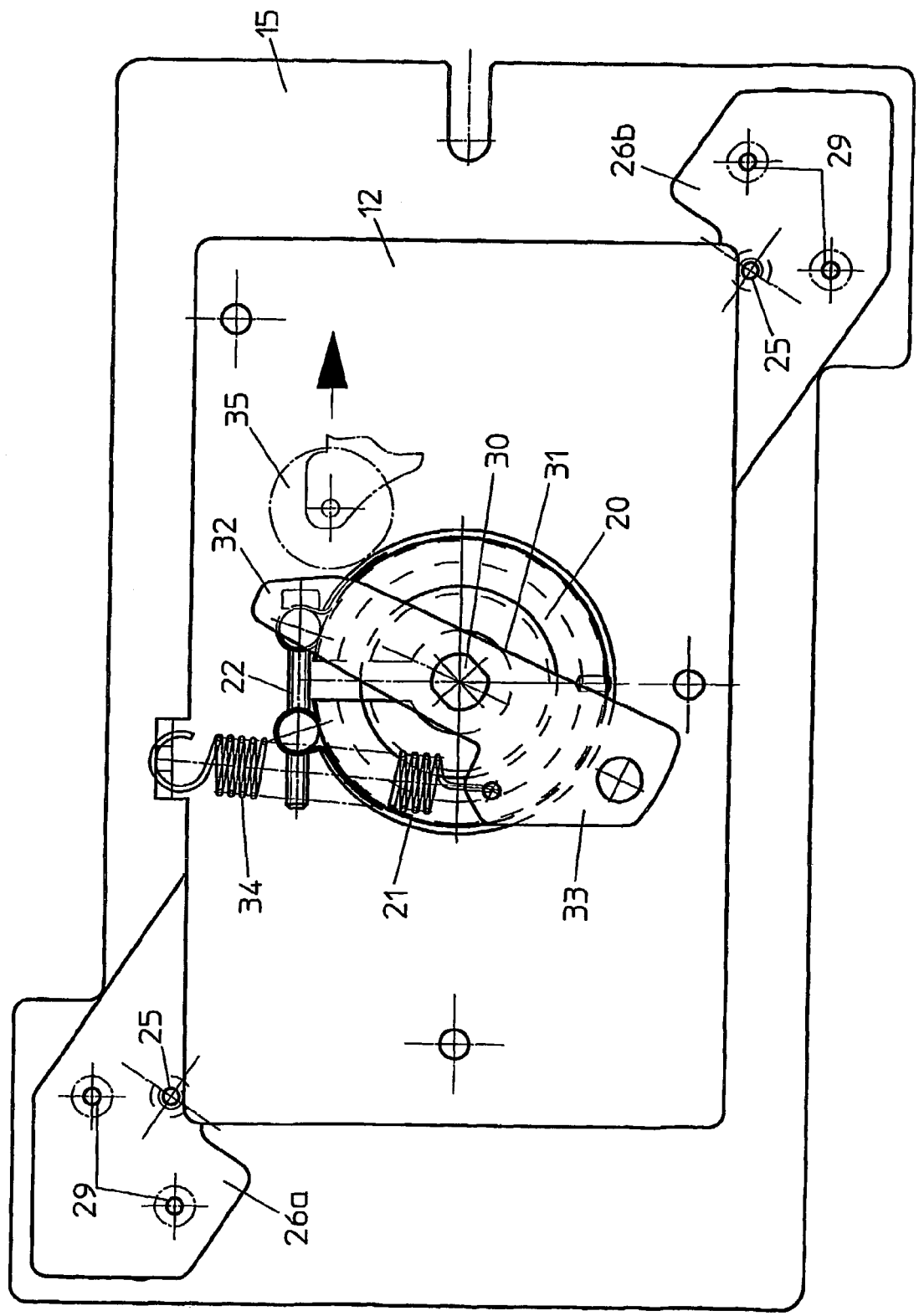
FIG. 7a shows a bottom view of the support according to the present invention with a locked microtiter plate.

The coupling lever 24 is seated on a perpendicular shaft 30, whose upper end is rotatably attached centrally on the lower side of the support plate 15 and which is guided further through the hole 17 (FIG. 2) in the ball 16 and connecting piece 18. Directly adjoining the end of the connecting piece 18 (see FIG. 7a), the shaft 30 carries an operating lever 31 as an operating part, having a free first arm 32 and a second arm 33, upon which a spiral spring 34 anchored on the bearing plate 12 engages. This spring exerts a pull on the operating lever 31, which holds the lever, and therefore, via the shaft 30, also the coupling lever 24 and the sliders 26a, b, in the locking position (FIGS. 6a, 7a), in which the centering stops press against the edge of the microtiter plate 4, one corner of the microtiter plate 4 lying between each two points which the two centering heads 23 of a centering stop touch.

Figure 6B:
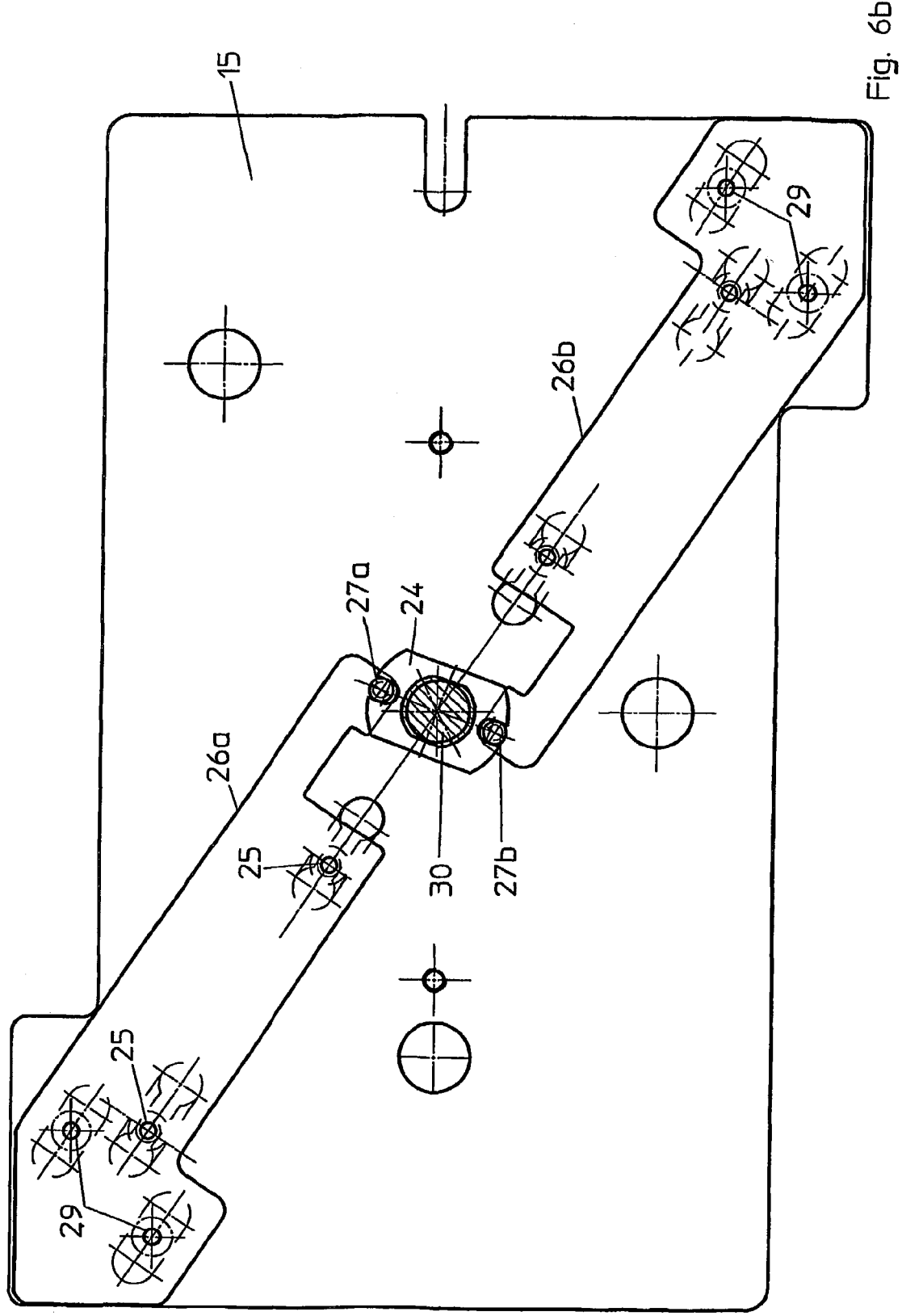
FIG. 6b shows a section through the support according to the present invention corresponding to FIG. 6a, but with an unlocked microtiter plate.
Figure 7B:
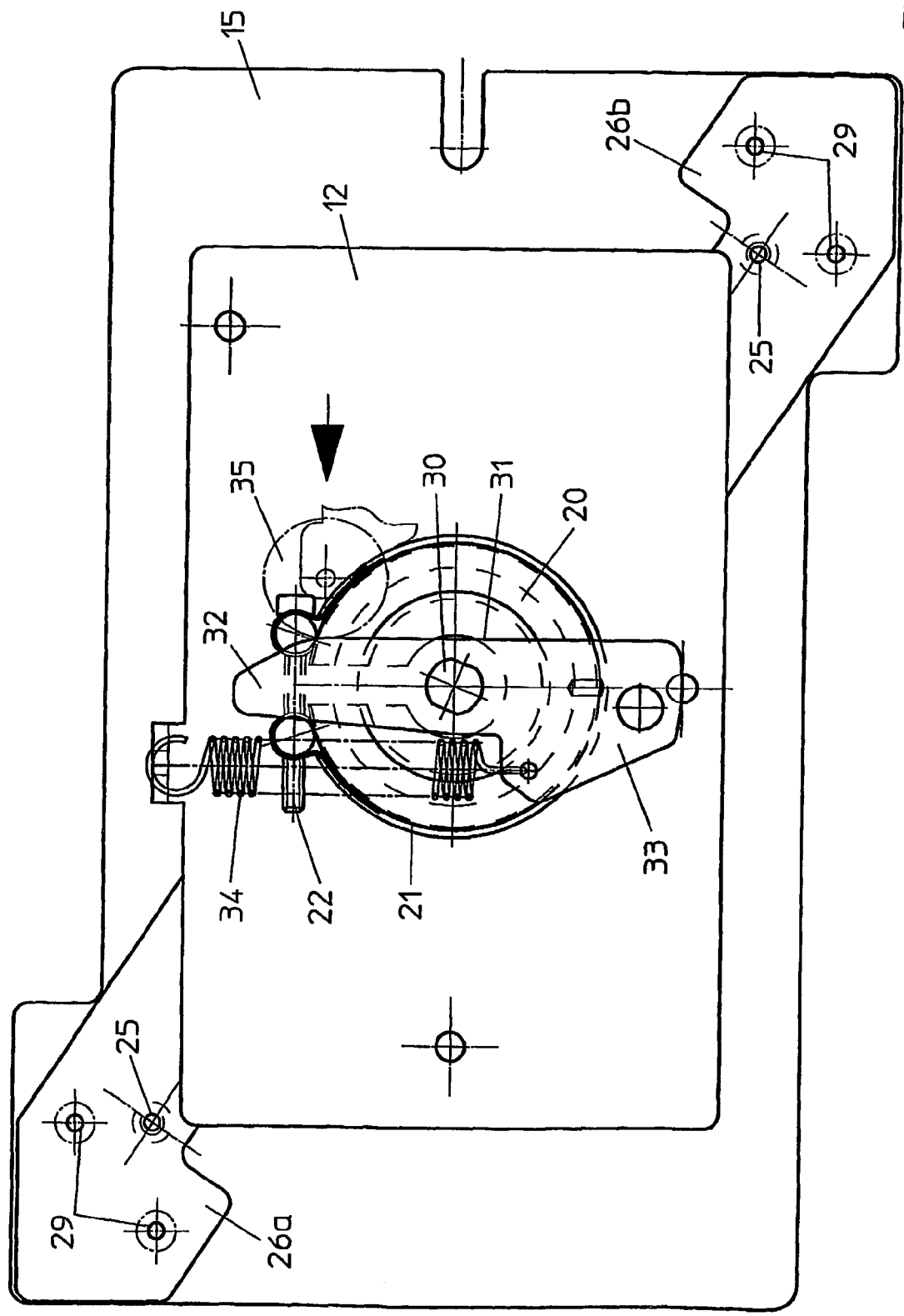
FIG. 7b shows a bottom view of the support according to the present invention corresponding to FIG. 7a, but with an unlocked microtiter plate.

If the operating lever 31 is now rotated against the returning force of the spiral spring 34 (counterclockwise in FIG. 7a), using, for example, an operating roller 35, which is extendably and retractably mounted on the table 1 and acts on its first arm 32, or another operating element or even operating stop, then the sliders 26a, b are pushed outward, through rotation of the coupling lever 24 in the same direction, into an unlocking position (FIGS. 6b, 7b) in which the centering stops assume at least approximately their outer limit position, in which they are clear of the edge of the microtiter plate. They are therefore not in the way when the microtiter plate is lifted off the support plate 15 using the manipulator 5, for example, and another microtiter plate is placed on the support plate.

As soon as the action on the operating lever 31 ceases, it is pulled back into its basic position by the returning force of the spiral spring 34, which causes a corresponding rotation of the coupling lever 24 and causes the centering stops to be pushed back toward the centerpoint of the support plate 15, the microtiter plate placed on the support plate being pushed and rotated by the centering stops as far as necessary until the centering stops press against the edges of the microtiter plate on both sides and it is completely centered.

LIST OF REFERENCE NUMBERS

| | | | |
|---|---|---|---|
| 1 | table | 21 | clip |
| 2 | slide block | 22 | fixing screw |
| 3 | support | 23 | centering head |
| 4 | microtiter plate | 24 | coupling lever |
| 5 | manipulator | 25 | guide pin |
| 6 | pipetting head | 26a, b | sliders |
| 7 | support profile | 27a, b | carrier pins |
| 8 | support roller | 28 | slot |
| 9 | guide roller | 29 | shank |
| 10 | guide rail | 30 | shaft |
| 11 | cover profile | 31 | operating lever |
| 12 | bearing plate | 32 | first arm |
| 13 | socket | 33 | second arm |
| 14 | opening | 34 | spiral spring |
| 15 | support plate | 35 | operating roller |
| 16 | ball | | |
| 17 | hole | | |
| 18 | connecting piece | | |
| 19 | stop | | |
| 20 | clamping ring | | |

What is claimed is:

1. A support for a microtiter plate or the like, having a base and a support plate, which is connected to the base via a fixable ball and socket joint so the support plate may be tipped and/or rotated in a limited way, a center of rotation of the ball and socket joint lying at the height of the upper side of the support plate, the ball and socket joint comprising:
    a socket which is connected to the base,
    a ball which is mounted in the socket and connected to the support plate, wherein the outer surface of the ball, shaped like a partial sphere and the correspondingly shaped inner surface of the socket are in permanent snug contact,
    a connecting piece shaped onto a lower side of the ball, which connecting piece projects through an opening of the socket and supports a stop and which connecting piece is an extension of the ball that is implemented in one piece together with the ball and that is shaped onto the ball's lower side, and
    a clamping part supported on said stop, which clamping part presses against the outside of the socket and is pressed against the socket to fix the ball and socket joint.

2. The support of claim 1, wherein the stop is implemented as annular and the clamping part is implemented as a clamping ring.

3. The support of claim 2, wherein the clamping ring is made of an elastic material and is enclosed by a clip, which may be tensioned to press the ring against the socket.

4. The support of claim 3, wherein the clip may be tensioned using a fixing screw.

5. The support of claim 1, wherein the ball and the connecting piece have a vertical central through hole, in which a perpendicular shaft is rotatably guided; said perpendicular shaft supporting a coupling lever in the region of its upper end and an operation part in the region of its lower end; the coupling lever at diametrically opposite points engaging two sliders that are movable diagonally under the support plate, each slider carrying one centering stop at an outer end; the two centering stops being on the upper side of the support plate, lying opposite one another at a distance, and being movable diametrically opposite one another away from a centerpoint lying centrally between them along a diagonal of the support plate.

6. The support according to claim 5, wherein each centering stop comprises a pair of centering heads which are at a distance to one another transverse to the movement direction.

7. The support of claim 6, wherein the centering heads each taper conically downward.

8. The support of claim 5, wherein the centering stops are movable by actuating an operating part positioned on the bottom side of the support.

9. The support of claim 5, wherein the operating part is implemented as an operating lever attached to the shaft.

10. The support of claim 5, wherein the movement of the centering stops away from the centerpoint acts against an elastic returning force.

11. The support according to claim 10, wherein the returning force is produced by a spring, which engages on the operating lever.

12. The support of claim 1, wherein the socket has an inner surface, which corresponds to an outer surface of the ball that is shaped like a partial sphere, and wherein the socket has an outer surface that tapers against the opening where the connecting piece of the ball projects through the socket.

13. The support of claim 12, wherein the socket is shell shaped and the socket has an outer surface close to the opening, where the connecting piece of the ball projects through the socket, which runs essentially parallel to an inner surface of the socket.

14. The support of claim 1, wherein the ball with the connecting piece is made of plastic, and wherein the socket is made of a metal.

* * * * *

UNITED STATES PATENT AND TRADEMARK OFFICE
CERTIFICATE OF CORRECTION

| | |
|---|---|
| PATENT NO. | : 7,054,001 B2 |
| APPLICATION NO. | : 10/362257 |
| DATED | : May 30, 2006 |
| INVENTOR(S) | : Alfred Geiger |

It is certified that error appears in the above-identified patent and that said Letters Patent is hereby corrected as shown below:

(73) Assignee: Tecan Trading AG, Männedorf (CH)

Signed and Sealed this

First Day of August, 2006

JON W. DUDAS
*Director of the United States Patent and Trademark Office*